(12) United States Patent
Lam et al.

(10) Patent No.: US 11,141,300 B2
(45) Date of Patent: Oct. 12, 2021

(54) PUSHABLE IMPLANT DELIVERY SYSTEM

(71) Applicant: Terumo Corporation, Tokyo (JP)

(72) Inventors: Cang Lam, Tustin, CA (US); Shirley Vong, West Covina, CA (US); Greg Kelley, Santee, CA (US)

(73) Assignee: Terumo Corporation, Tokyo (JP)

( * ) Notice: Subject to any disclaimer, the term of this patent is extended or adjusted under 35 U.S.C. 154(b) by 224 days.

(21) Appl. No.: 16/407,018

(22) Filed: May 8, 2019

(65) Prior Publication Data

US 2019/0262155 A1 Aug. 29, 2019

Related U.S. Application Data

(63) Continuation of application No. 15/269,823, filed on Sep. 19, 2016, now Pat. No. 10,322,020.

(60) Provisional application No. 62/220,918, filed on Sep. 18, 2015.

(51) Int. Cl.
| | | |
|---|---|---|
| *A61F 2/966* | (2013.01) | |
| *A61F 2/82* | (2013.01) | |
| *A61F 2/962* | (2013.01) | |
| A61F 2/88 | (2006.01) | |
| A61F 2/95 | (2013.01) | |

(52) U.S. Cl.
CPC ............... *A61F 2/966* (2013.01); *A61F 2/82* (2013.01); *A61F 2/88* (2013.01); *A61F 2/9517* (2020.05); *A61F 2002/9665* (2013.01); *A61F 2230/0069* (2013.01)

(58) Field of Classification Search
CPC .... A61F 2/95; A61F 2/966; A61F 2002/9665; A61F 2/954; A61F 2/2427–2/2439; A61B 25/104; A61B 2025/2045; A61B 2025/1045
See application file for complete search history.

(56) References Cited

U.S. PATENT DOCUMENTS

| | | | |
|---|---|---|---|
| 5,824,041 A | 10/1998 | Lenker et al. | |
| 6,623,518 B2 | 9/2003 | Thompson et al. | |
| 6,776,791 B1 | 8/2004 | Stallings et al. | |
| 6,936,058 B2 | 8/2005 | Forde et al. | |
| 7,309,351 B2 | 12/2007 | Escamilla et al. | |
| 8,926,693 B2 * | 1/2015 | Duffy ...................... | A61F 2/966 623/2.11 |
| 2001/0049549 A1 | 12/2001 | Boylan et al. | |
| 2002/0016597 A1 | 2/2002 | Dwyer et al. | |
| 2002/0055767 A1 | 5/2002 | Forde et al. | |
| 2002/0120322 A1 | 8/2002 | Thompson et al. | |
| 2002/0120323 A1 | 8/2002 | Thompson et al. | |
| 2006/0111771 A1 | 5/2006 | Ton et al. | |
| 2007/0100423 A1 * | 5/2007 | Acosta ...................... | A61F 2/91 623/1.11 |
| 2008/0300667 A1 | 12/2008 | Hebert et al. | |

(Continued)

FOREIGN PATENT DOCUMENTS

WO  WO2007/134290 A2  11/2007

*Primary Examiner* — Katherine H Schwiker
*Assistant Examiner* — Brigid K Byrd
(74) *Attorney, Agent, or Firm* — Inskeep IP Group, Inc.

(57) ABSTRACT

An implant delivery system is described, having a distal tip and outer sheath that remain in a fixed position during implant delivery. A pusher mechanism within the sheath pushes an implant out of a gap between a distal end of the sheath and the distal tip.

15 Claims, 6 Drawing Sheets

(56) References Cited

U.S. PATENT DOCUMENTS

| | | |
|---|---|---|
| 2010/0030255 A1* | 2/2010 | Berra ............... A61F 2/848 606/200 |
| 2011/0224744 A1 | 9/2011 | Moffitt et al. |
| 2013/0006348 A1* | 1/2013 | Kusleika ............ A61F 2/95 623/1.12 |
| 2013/0131775 A1* | 5/2013 | Hadley ............ A61F 2/966 623/1.11 |
| 2013/0226278 A1 | 8/2013 | Newell et al. |
| 2013/0245745 A1 | 9/2013 | Vong et al. |
| 2013/0245754 A1 | 9/2013 | Blum et al. |
| 2014/0200648 A1 | 7/2014 | Newell et al. |

* cited by examiner

PUSHABLE IMPLANT DELIVERY SYSTEM

RELATED APPLICATIONS

This application is a continuation of and claims priority to U.S. patent application Ser. No. 15/269,823 filed Sep. 19, 2016 entitled Pushable Implant Delivery System, which claims benefit of U.S. Provisional Application Ser. No. 62/220,918 filed Sep. 18, 2015 entitled Pushable Implant Delivery System, both of which are hereby incorporated herein by reference in their entireties.

BACKGROUND OF THE INVENTION

Medical implants such as stents or stent grafts can be used to open blood vessels to mitigate the effects of plaque buildup, as a scaffold to keep embolic material within an aneurysm, as a flow diverter to limit blood flow to certain regions, or for other reasons.

Some implant delivery systems have an outer tubular sheath that contains an elongated "pusher" member on which the implant is disposed. When the distal end of the outer tubular sheath reaches its desired target site, the pusher member can be distally advanced to "push" the implant out of the sheath. In many of these types of delivery systems, the implant is disposed over a portion of the pusher and the pusher further comprises a distal end portion located at or near the distal end of the catheter sheath.

In that regard, as the pusher is distally advance to deploy the implant, the pusher's distal end is advanced well beyond the distal end of the sheath. Depending on the shape and size of the vessel distal of the target site, such distal movement may cause the pusher to contact portions of the vessel beyond the deployed implant. Such contact may result in complications and therefore can be undesirable.

SUMMARY OF THE INVENTION

An implant delivery system is described. The implant delivery system can be used for a stent and/or stent graft and/or other implants such as coils, plugs, occluders, or other implants.

One embodiment is directed to a delivery system for a vascular implant, such as a stent, having a pushing mechanism configured to push the stent out of the end of an outer catheter sleeve or sheath without further advancing any portions of the pushing mechanism distally beyond the deployed stent. In other words, even as the stent is deployed, the distal end member of the delivery system remains in a fixed location relative to the outer sheath and the vascular target site in the patient. In this respect, undesirable contact distal of the deployed implant may be reduced or eliminated.

In one embodiment an implant delivery system includes an inner tube and a pusher element.

In another embodiment an implant delivery system includes an inner tube and a pusher element where the pusher element travels over the inner tube.

In another embodiment an implant delivery system includes an inner tube with a fixed position.

In another embodiment an implant delivery system includes an inner tube where the inner tube facilitates placement of a guidewire.

In another embodiment an implant delivery system includes an inner tube with an enlarged distal section.

In another embodiment an implant delivery system includes a pusher element where the pusher element contains one or more recesses to accommodate an implant.

In another embodiment an implant delivery system is used to deliver a stent and/or stent graft.

In another embodiment an implant delivery system is used to deliver a stent and/or stent graft and includes a pusher element. The stent and/or stent graft has a structure which engages with one or more recesses on the pusher element.

In another embodiment an implant delivery system includes a guidewire and a pusher element.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
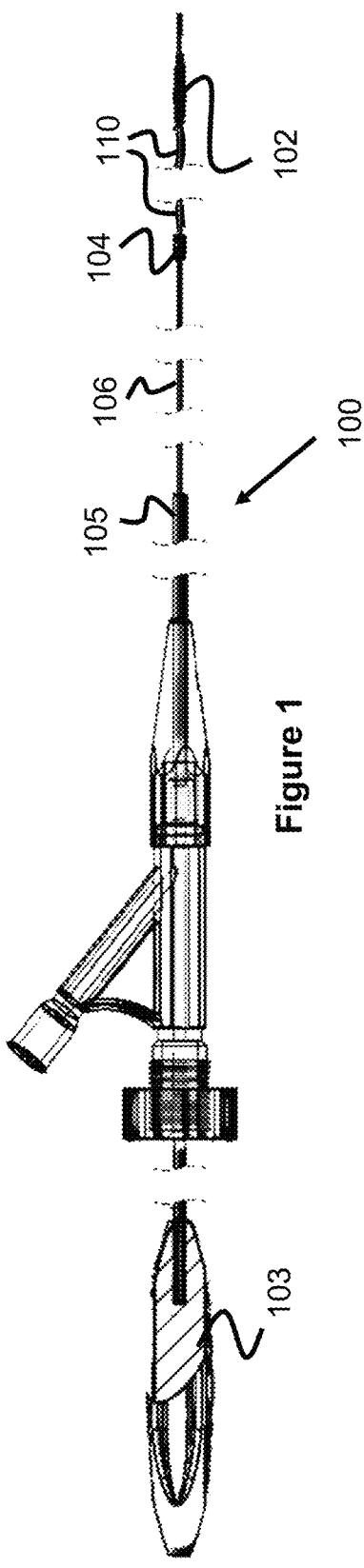
FIG. 1 illustrates a side view of an implant delivery system with a fixed distal end according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-4 illustrate a delivery system 100 for a vascular implant, such as a stent 110, having a pushing mechanism configured to push the stent 110 out of the end of an outer catheter sleeve or sheath 105 without further advancing any portions of the pushing mechanism or other components distally beyond the deployed stent. In other words, even as the stent 110 is deployed, the distal end member 102 of the delivery system 100 remains in a fixed location relative to the outer sheath 105 and the vascular target site in the patient. In this respect, undesirable contact distal of the deployed implant may be reduced or eliminated.

Figure 2:
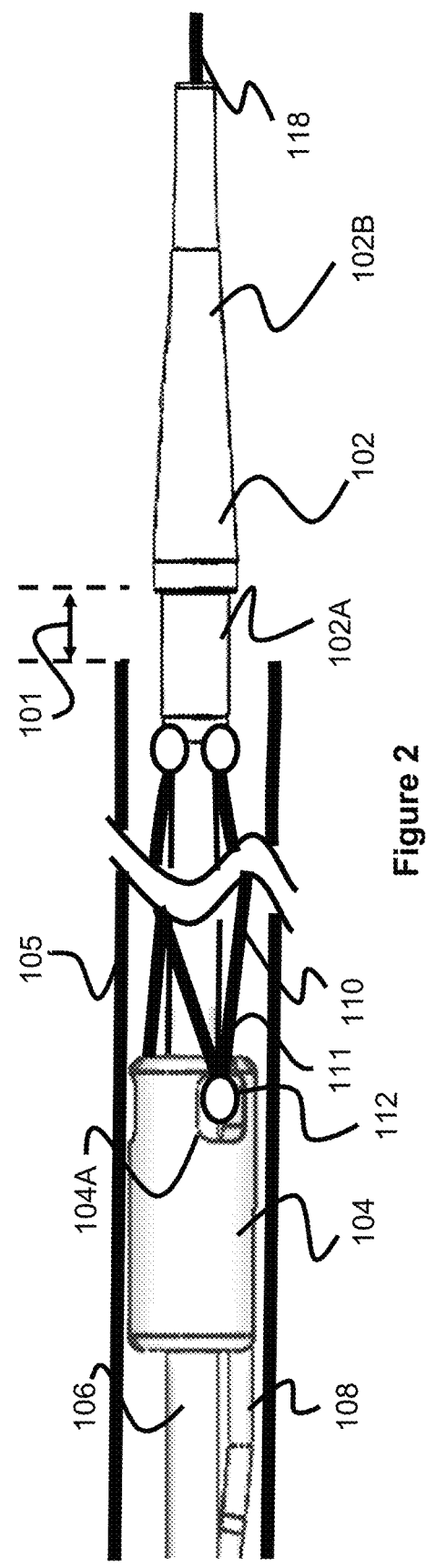
FIG. 2 illustrates a magnified view of a distal end of the delivery system of FIG. 1.

As best seen in FIG. 2, the delivery system 100 includes an elongated tube 106 that extends between the proximal and distal ends of the delivery system 100. The proximal end of the elongated tube 106 is fixed in a non-retractable manner relative to the proximal components of the delivery system 100 and terminates distally with the distal end member 102. In this respect, once the delivery system 100 is advanced to a desired location within a patient, the elongated tube 106 and the distal end member 102 remain at that location during delivery, moving only when the entire delivery system is withdrawn from the patient.

Preferably, the outer sheath 105 is similarly fixed in a non-retractable manner relative to the proximal components of the delivery system 100. In other words, the sheath 105 maintains a fixed position relative to the tube 106 and distal end member 102. In that regard, the distal end of the sheath 105 is positioned a proximal distance from the distal end member 102 (or from the largest part of the distal end member 102) so as to create a circumferential gap 101 through which the stent 110 can be pushed through (see FIGS. 3 and 4). Since the outer sheath 105 and distal end member 102 are fixed from moving relative to each other, the circumferential gap 101 remains present through all phases of the delivery process.

In an alternate embodiment, the sheath 105 can be axially movable relative to the distal end member 102, allowing a portion of the stent 110 to be exposed.

The stent 110 is pushed out of the delivery system 100 by a sliding pusher element 104 that has an internal passage through which the elongated tube 106 is disposed. The pusher element 104 can therefore slide axially along a portion of the tube 106 without also moving the tube 106, distal end member 102, or sheath 105. In other words, the pusher element 104 is independently moveable, allowing the tube 106, distal end member 102, and sheath 105 to have fixed lengths. The pusher element 104 also releasably connects to a proximal end of the stent 110, which allows the pusher element 104 to distally push the stent 110, but also proximally retract the stent 110 prior to its full release and deployment.

Figure 5:
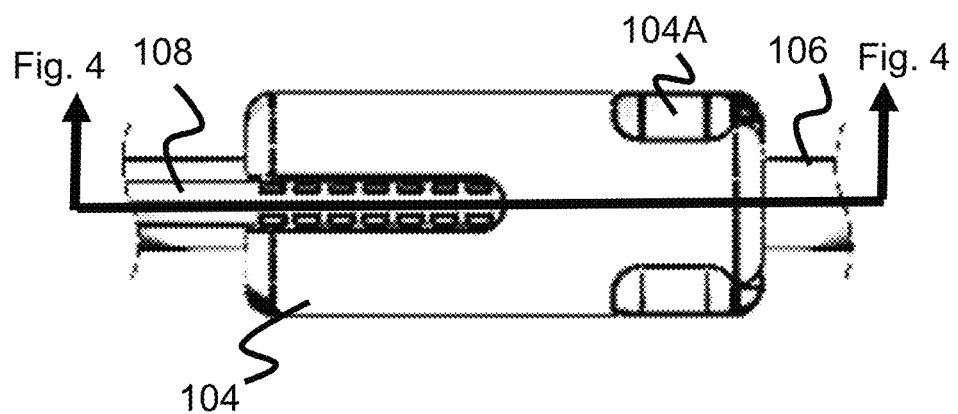
FIGS. 5-7 illustrate various views of a sliding pusher element of the delivery system of FIG. 1.
Figure 6:
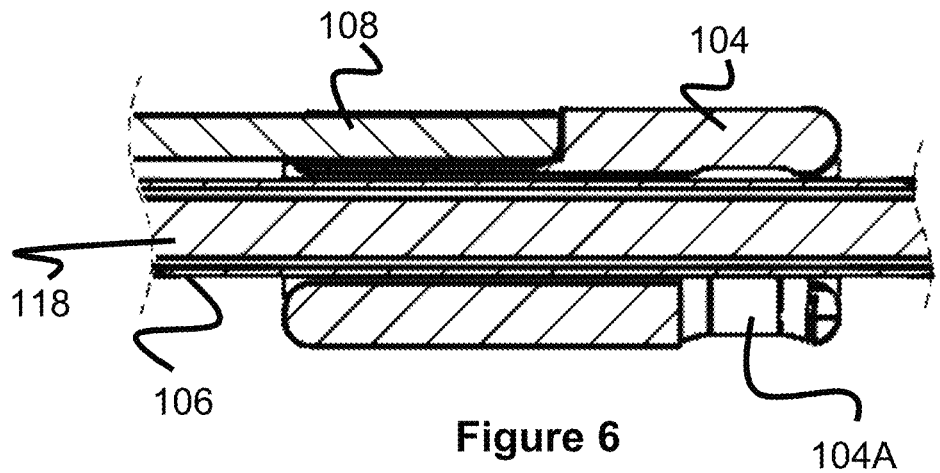
Figure 7:
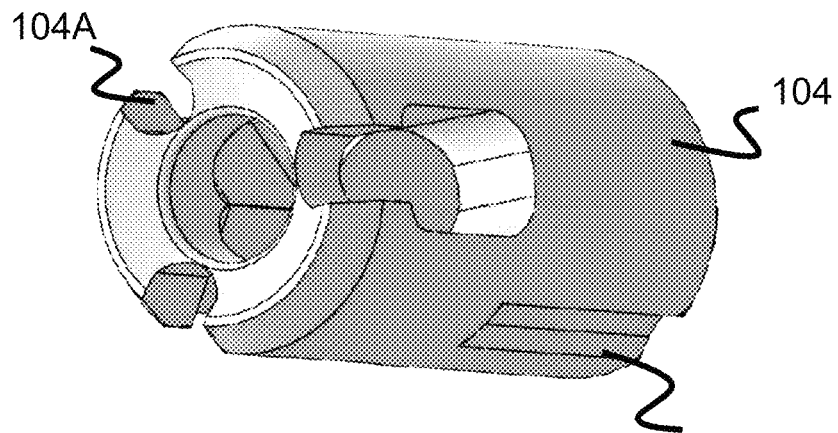

Referring to FIGS. 5-7, in one embodiment, the stent 110 releasably connects to the pusher element 104 by enlarged bulbs 112 that are fixed on the proximal end of the stent 110 (such as on the proximal ends of stent loops 111) and that fit into apertures or depressions on the outer surface of the pusher element 104. The sheath 105 maintains the bulbs 112 in the depressions 104A, further preventing radial expansion of the stent 110. When the pusher element 104 moves distally beyond the distal end of the outer sheath 105, the proximal end of the stent 110 expands, allowing the bulbs 112 to move out of the depressions 104A and thereby disengage from the pusher element 104. In one embodiment, the depression 104A is somewhat oversized relative to the bulbs 112 size, allowing for some "play" or movement within the depression 104A.

The depression 104A preferably provides only an axial restraint to the bulb 112. If the depression 104A is large enough, the bulb 112 may also have some vertical movement (perpendicular relative to the axis of the device). However, preferably the overall clearance is limited in order to limit the amount of wasted energy involved in pushing and pulling the implant delivery device 100, as well as to limit the amount of jostling the stent 110 undergoes during delivery.

Radially, the bulb 112 and stent 110 are restrained by the sheath 105 rather than depression 104A. However, other embodiments can utilize a radial limitation within the depression 104A. For example, the depression 104A can take on the shape of a partial sphere with an outward projection (e.g., a partial egg-shape) to restrict the bulb 112 movement in a radial as well as an axial direction.

Figure 8:
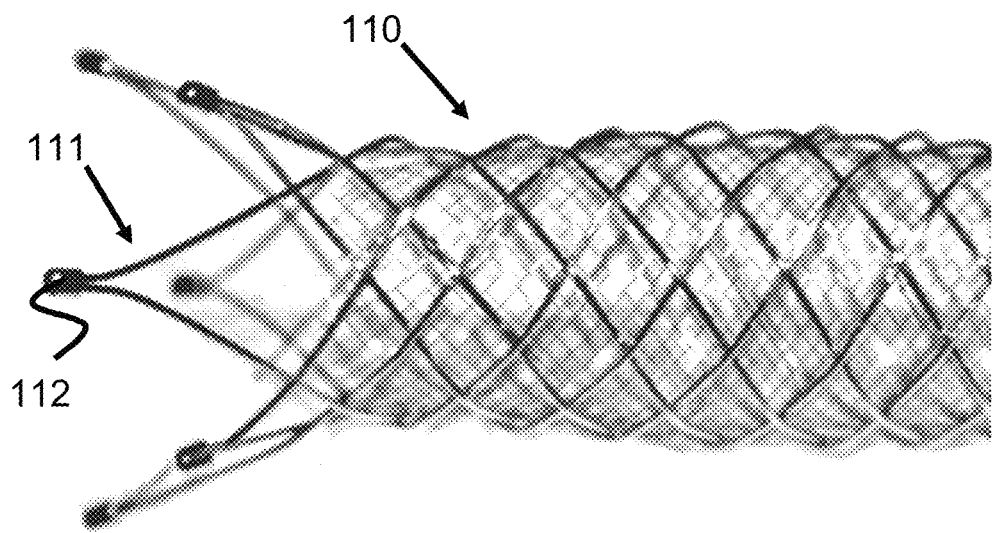
FIG. 8 illustrates an example stent that can be used with the delivery system of FIG. 1.

The stent 110 can be seen further in FIG. 8 and additional details of the bulbs 112 and its alternatives can be found in U.S. application Ser. No. 15/268,379, which is incorporated herein by reference. In one embodiment, the stent 110 (or stent-graft) is comprised of a mesh of wires. In one embodiment the implant is a stent or stent-graft comprised of a mesh of wires and comprising two layers—an inner layer and an outer layer. The wire meshes end at the proximal and distal ends of the stent leaving open pairs of wire ends. Cap or bulbs 112 may be placed over these open wire ends to secure the open ends and to prevent the open ends from traumatizing the vessel. Alternatively, instead of a cap, the wires may be welded together. The weld shape would be geometrically similar to bulbs 112. The cap can take on a number of shapes besides the shape shown in FIG. 8; a non-exhaustive list of examples includes circular, ovular, prism, pyramidal, ellipsoid, and hemispherical. Alternative embodiments for the bulbs 112 involve configurations where there is a cylindrical base to wrap around the wires and a proximal 'top' structure which can be screwed, affixed, glued, or welded onto the base. The 'top' structure would thus physically cover the proximal ends of the wires.

In one embodiment, the bulbs 112 of the stent 110 are all located at the same radial position relative to each other. In another embodiment, some of the bulbs 112 are longitudinally offset from each other.

The pusher element 104 is axially moved by a connection to a physician-actuated pusher rod 108. The pusher rod 108 is connected to the pusher element 104 and to a handle 103 at the proximal end of the delivery device 100, allowing the physician to move the handle 103 proximally or distally to thereby move the pusher element 104 proximally or distally. In one embodiment, the pusher rod 108 connects to the pusher element 104 at a location that is radially offset from a center of the pusher element 104, allowing the tube 106 to pass through the center of the pusher element 104 (seen in FIGS. 5-7).

The distal end member 102 preferably has an elongated, conical region 102B that proximally increases in diameter to reduce trauma as the delivery device 100 is advanced through the patient. The distal end member 102 also includes a reduced diameter region 102A that increases in diameter in the distal direction, which helps radially expand and direct outwards the distal end of the stent 110 as it is distally advanced within the sheath 105. Optionally, the very proximal portion of the distal end member 102 may also include depressions (similar to depressions 104A) that help maintain the position of the distal bulbs 112 prior to the commencement of the stent 110 deployment. While only three depressions 104A are illustrated, it is contemplated that other numbers of depressions 104A are also possible (e.g., between 1 and 16). Additionally, while the depressions 104A are all illustrated at the same longitudinal position, it is contemplated that some can be longitudinally offset from each other.

The presence of distal end member 102 provides a few benefits. First, it provides an atraumatic surface for minimizing blood vessel trauma during tracking within the vasculature, since the distal end member 102 is preferably made of a soft, polymeric material. Second, the distal end member 102 provides a ramping surface for the implant (i.e., region 102A). When the stent 110 is expelled from the sheath 105, it will open up relatively quickly since the stent 110 is kept in a restrained state due to the compressive force of the sheath 105. Many implants are made of a shape memory material, so they quickly adopt their expanded configuration when released from a sheath 105. Instead of an abrupt opening, the region 102A provides a ramped, controlled opening as the inner surface of the stent 110 contacts the region 102A while the stent 110 is pushed out. Such a controlled delivery is also beneficial to aid retraction. The tendency of an implant to adopt its expanded configuration can result in an abrupt implant opening and therefore the user may not be able to pull the stent back after advancing to a certain point, prohibiting repositionability. As an example, once the majority of the stent 110 is expanded, the opening force can transmit through the rest of the stent 110, propelling it in premature delivery. If the implant opens and is delivered too quickly, there is little time to reposition the implant once a portion of the implant opens. A more controlled delivery therefore allows the user more time and control throughout the delivery process.

Figure 9:
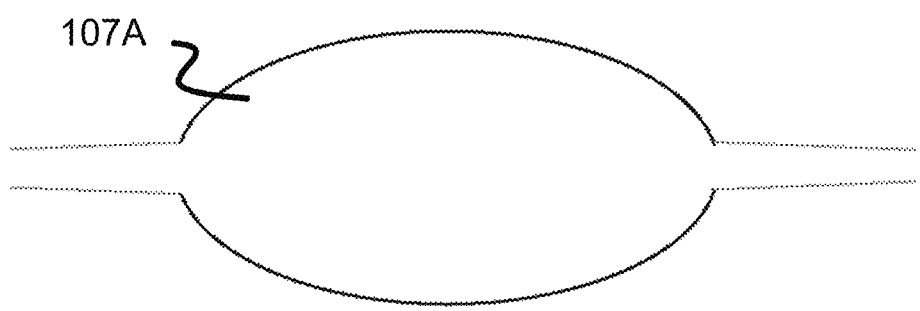
FIGS. 9 and 10 illustrate alternate embodiments of distal end members according to the present invention.
Figure 10:
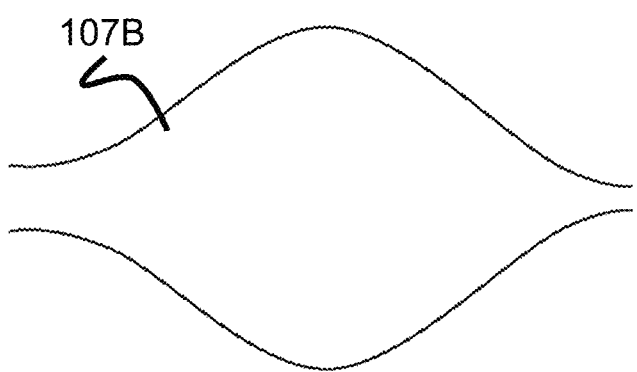

The proximal region 102A of distal end member 102 preferably has a relatively abrupt transition region as shown in FIG. 2. However, this region 102A can be varied to create a region with a larger or a smaller taper. The remaining portions of the distal end member 102 may have a relatively consistent diametrical profile or may gradually taper to a smaller diameter as shown in FIG. 2. Other variations are possible, including abrupt tapering to a smaller diameter and/or larger diameter region. A gradual taper to a smaller diameter may be desirable to limit the potential contact surface area between distal end member 102 and the blood vessel, while also providing an atraumatic contact surface between the delivery system 100 and the vasculature. Other shape possibilities are shown in FIGS. 9 and 10, such as an ovular or balloon-like shape 107A, or a football-like shape 107B. Various other shapes are possible for the overall profile of distal end member 102.

Figure 11:
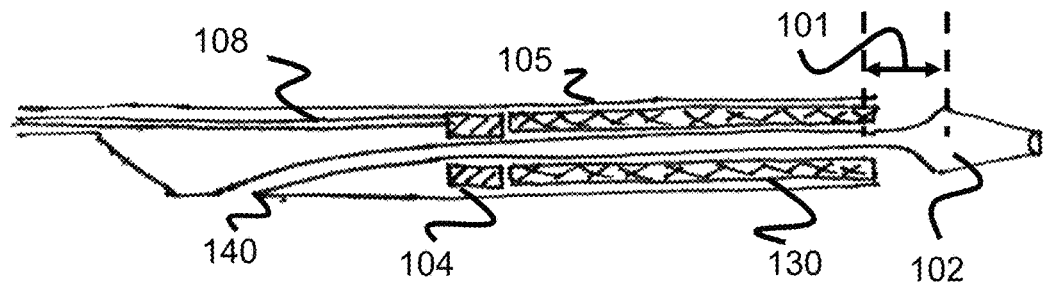
FIGS. 11 and 12 illustrate alternate embodiments of an implant delivery system according to the present invention.
Figure 12:
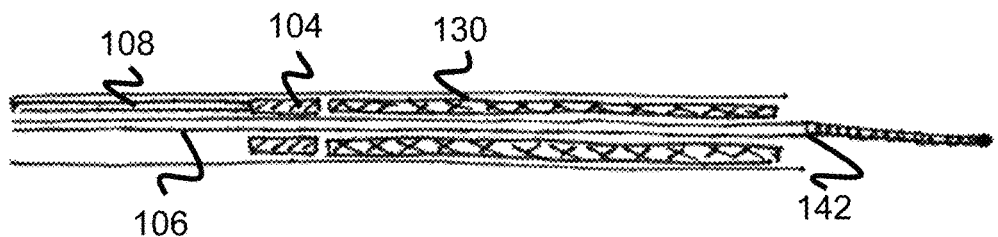

The tube 106 and distal end member 102 preferably form a connected passage within their structure that extends from the proximal portion of the delivery device 100 and terminates at the distal end of the distal end member 102. This passage allows the delivery device 100 to be tracked over a guidewire 118 that has been placed at the target delivery location within the patient (see FIG. 2). Alternately, the proximal end of the passage may terminate distally of the proximal portion of the delivery device 100, creating a rapid exchange port 140 for "over-the-wire" use (see FIG. 11). In another alternate embodiment, the passage can be used with an atraumatic wire 142, instead of or in addition to the distal end member 102 (FIG. 12).

Figure 3:
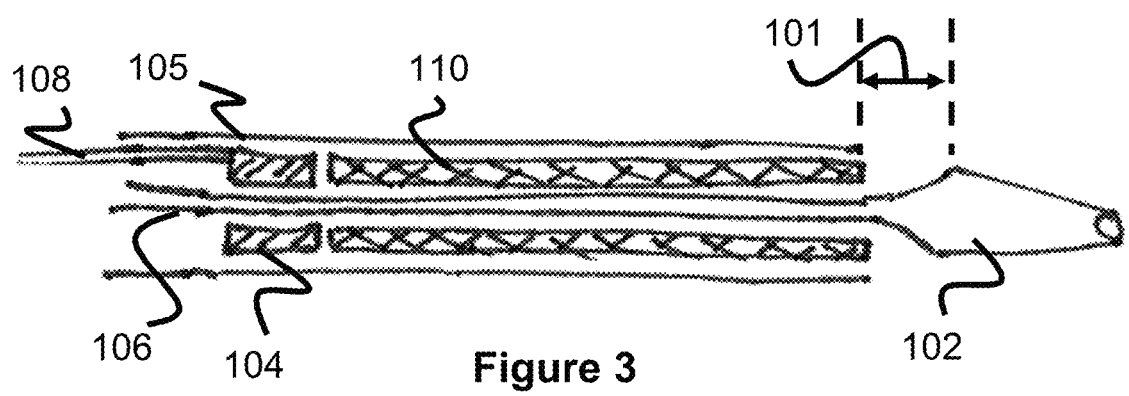
FIGS. 3 and 4 illustrate side views of the delivery system of FIG. 1 deploying a stent.
Figure 4:
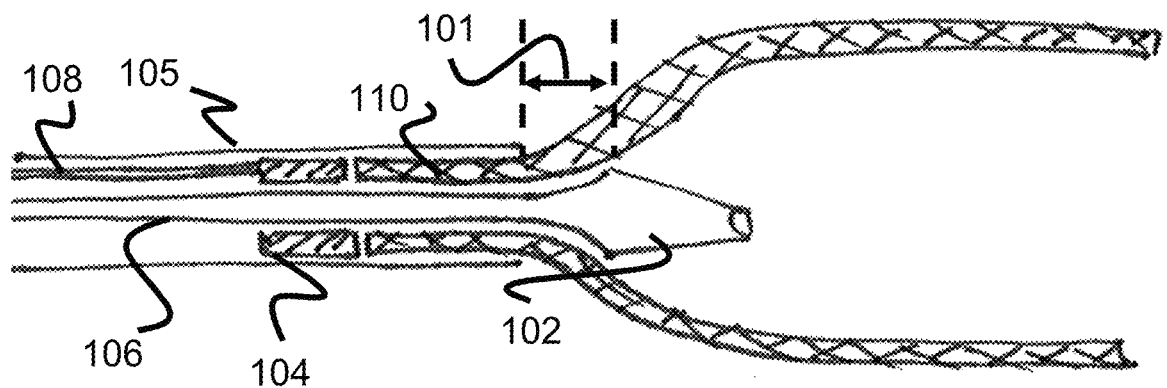

In FIGS. 3 and 4, the simplified views of the delivery system 100 illustrate the operation for delivering the stent 110. First, a guidewire 118 is placed at or near a desired target location within the vasculature of a patient. Next, the delivery device 100 is tracked over the guidewire 118 such that the guidewire 118 passes through the passage of the distal end member 102 and tube 106. Once the distal end of the delivery device 100 is positioned at or near the target location, the physician proximally advances the handle 103, thereby distally moving the pusher rod 108, the pusher element 104, and the stent 110, while the tube 106, distal end 102 and outer sheath 105 remain in relatively fixed positions. As the distal end of the stent 110 moves forward, the tapered or conical portion 102A of the distal end member 102 helps direct the stent 110 out through the gap 101 between the distal end of the sheath 105 and the largest diameter portion of the distal end member 102.

Prior to the enlarged bulbs 112 of the stent 110 leaving the sheath 105, the physician may decide to retract the stent 110 back into the delivery device 100 through gap 101 and redeploy to better achieve a desired stent 110 position. The handle 103 can be retracted proximally, causing the pusher rod 108, the pusher element 104, and the stent 110 to move proximally, recapturing the stent 110 back within the sheath 105. Finally, the stent 110 can be redeployed as noted above until the distal end of the stent 110 (e.g., the bulbs 112) have escaped the sheath 105.

Figure 13:
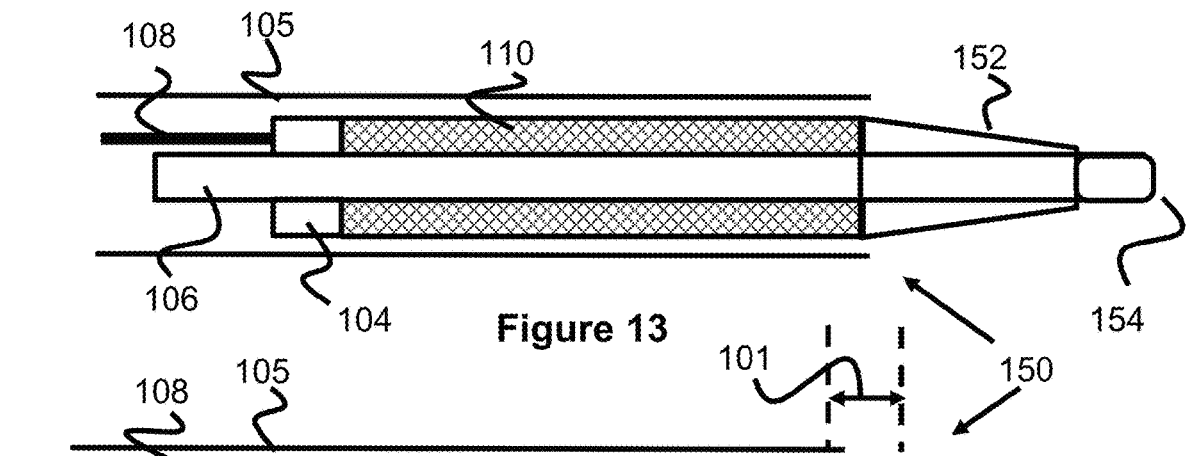
FIGS. 13-16 illustrate an alternate embodiment of an implant delivery system having a sliding tip member according to the present invention.
Figure 14:
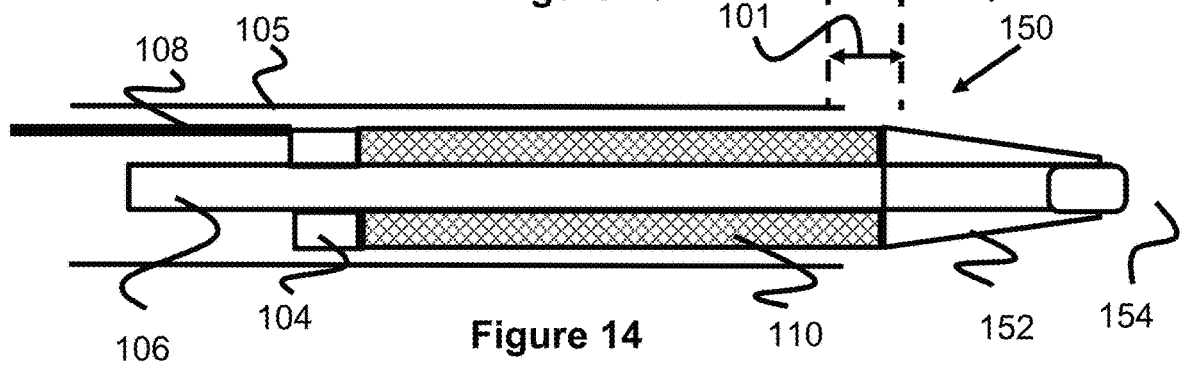

FIGS. 13-16 are directed to an alternate embodiment of a delivery system 150 that is generally similar to the previously described delivery system 100. However, the system 150 includes a distal tip member 152 that is connected to a distal end of the stent 110 and slides distally during a deployment procedure. In this regard, the system 150 can be delivered with the tip member 152 maintaining the distal end of the sheath 105 in a closed position, as seen in FIG. 13. As the stent 110 is pushed distally, it pushes the distal tip member 152 distally, creating the gap 101 between the sheath 105 and the tip member 152 through which the stent 110 is deployed, as seen in FIG. 14.

Figure 16:
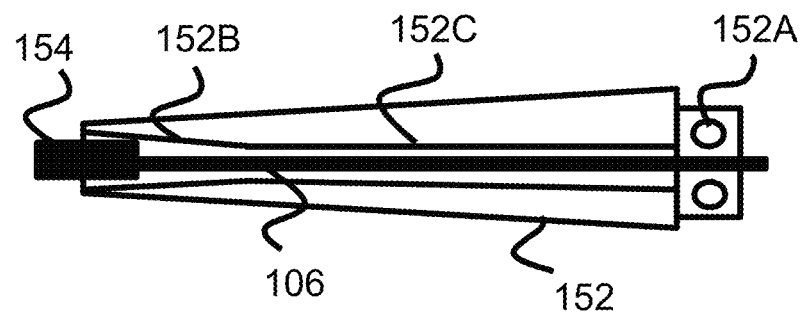

The distal tip member 152 is prevented from moving off the distal end of the tube 106 by stopper 154, which is fixed to the tube 106. As best seen in FIG. 16, the distal tip member 152 has an interior passage having a distal, larger diameter region and a proximal, smaller diameter region. The stopper 154 can pass into the larger diameter region 152B but is too large for the smaller diameter region 152C, thereby preventing the distal tip member 152 from moving further. The stopper 154 has a generally cylindrical shape, but may alternately have a conical shape that decreases in the proximal direction.

Figure 15:
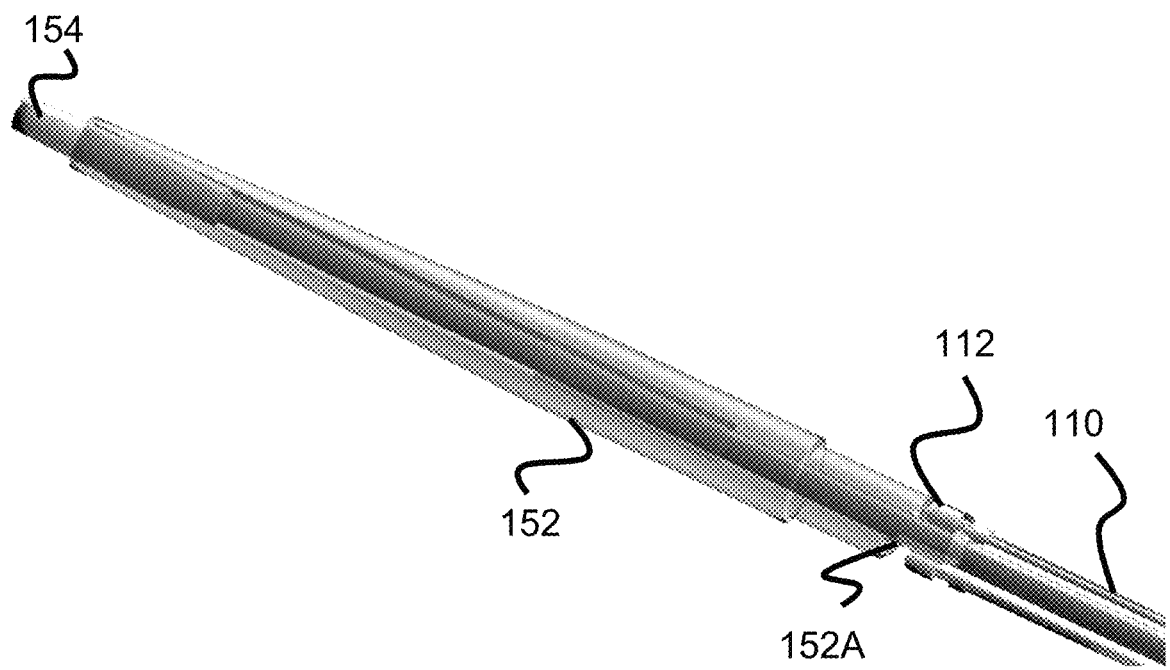

As best seen in FIG. 15, the proximal end of the tip member 152 includes a plurality of depressions 152A or surfaces to help engage the bulbs 112 on the distal end of the stent. As the stent 110 is distally advanced, the bulbs 112 contact and push the tip member 152 until the stopper 154 is reached.

In one example, the inner tube 106 can be comprised of a polymer. In another example, the inner tube 106 is metallic.

In one embodiment, the maximum outer diameter of distal end member 102 is equal to or larger than the inner diameter of sheath 105. In one example, the enlarged distal end portion 102, as well as the inner tube 106, are polymeric.

In another embodiment, the inner tube 106 is movable. In this embodiment, a user would separately manipulate the position of inner tube 106 and pusher element 104, since it may be desirable to allow the pusher element 104 to translate relative to the inner tube 106 to limit the amount of the inner tube 104 which is exposed outside the distal end of the sheath 105.

Alternate embodiments can utilize a shorter inner tube 106. The inner tube 106 could traverse only a portion of the overall delivery system length and the sheath 105 would utilize a proximal port to accommodate inner tube 106.

In one example, the overall working length (i.e. length from the proximal end of the sheath 105 to the distal tip of the distal end member 102) is about 90-150 centimeters, while the length of the rapid exchange embodiment (i.e. length from the proximal port 140—which is the starting point of inner tube 106—to the distal tip of the distal end member 102) is about 30-60 centimeters.

Other embodiments are also possible. For example, the pusher could utilize a screw or ratchet system. In this embodiment, the rod would be enclosed within another lumen. The rod and separate lumen would each contain corresponding male-female interfaces to support a ratcheting or screw-type system. The user would interact with knob at the proximal end of the system to push or pull the system. In one example, the knob is comprised of a dial which can be turned in one direction to advance the system and turned in another direction to retract the system. This system could also be automated via an electro-mechanical system where the knob could be turned in one direction to turn a motor to advance or push the system forward, and the knob could be turned in another direction to turn the system in another direction to retract the delivery system.

Pusher element 104 is shown as a round device which sits around inner tube 106. However, the pusher element 104 can take on a number of shapes. It need not completely sit around the inner tube 106 and may instead sit just around a portion of the tube 106 (e.g., a hemisphere). Alternatively, the pusher element 104 can take the form of a slider which slides solely on a circumferential portion of inner tube 106. Obviously, the smaller pusher element 104 is, the smaller the pusher element surface area will be which corresponds to fewer depressions 112 and/or retention structures to grasp the stent 110—however, a smaller pusher element 104 could be useful for a smaller implant where high retention strength is not necessary.

The implant delivery system can be used with a variety of implants, such as stent, stent/grafts, coils, plugs, occluders, etc. Though the system was primarily described with regards to stent and/or stent-grafts, the system can also be with several other devices. For example, the system could work with an embolic coil by having a distal coil implant structure and a connecting piece with an interface which connects to the pusher element 104 (similar to the bulb/depression arrangement of FIG. 2). A detachment mechanism would sit between the coil implant and connecting structure, where the connecting structure is thermally, mechanically, or electrolytically severed to effect delivery of the implant.

Though the term sheath or catheter is used in the specification to describe a delivery device which the implant delivery system is delivered through, the implant delivery system can also be tracked through various delivery devices such as hypotubes or other systems which can be used as a vascular conduit which an implant is delivered through.

Though the term inner tube is used to describe element 106 of the figures, the tube 106 can take on a number of different cross-sectional shapes including circular, ellipsoid, square, rectangular, prisms, etc. This list is meant to be non-exhaustive and illustrative.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vascular prosthesis delivery device comprising:
an inner tube accommodating a guidewire;
a prosthesis;
a pusher element movable over the inner tube, the pusher element accommodating a proximal portion of the prosthesis;
a tip member movable over the inner tube and having an interior passage, the tip member accommodating a distal portion of the prosthesis; and,
a distal enlargement positioned at a distalmost end of the inner tube;
wherein the passage of the tip member is configured to at least partially, distally pass over the distal enlargement and to limit further distal movement of the tip member during prosthesis delivery.

2. The vascular prosthesis delivery device of claim 1, wherein the pusher element has recesses accommodating the proximal portion of the prosthesis.

3. The vascular prosthesis delivery device of claim 1, wherein the tip member has recesses accommodating the distal portion of the prosthesis.

4. The vascular prosthesis delivery device of claim 1, wherein the distal enlargement is larger than a portion of the passage of the tip member.

5. The vascular prosthesis delivery device of claim 1, wherein the tip member is movable over the inner tube such that at least part of the tip member is positioned distally beyond the inner tube's distal enlargement.

6. The vascular prosthesis delivery device of claim 1, wherein the tip member has an outer proximal reduced diameter section sized to fit within an internal passage of a delivery sheath and an outer distal enlarged diameter region larger than the internal passage of the delivery sheath.

7. The vascular prosthesis delivery device of claim 1, wherein the tip member has an outer proximal reduced diameter section with recesses accommodating the distal portion of the prosthesis.

8. A vascular prosthesis delivery device comprising:
an inner tube accommodating a guidewire;
a prosthesis;
a pusher element movable over the inner tube, the pusher element accommodating a proximal portion of the prosthesis;
a tip member movable over the inner tube, the tip member accommodating a distal portion of the prosthesis; and
a distal enlargement located near a distal end of the inner tube;
wherein the tip member has a passage having a smaller inner diameter section and a larger inner diameter section, such that the larger inner diameter section is configured to distally move over the distal enlargement and the smaller inner diameter section is configured to limit further distal movement of the tip member during prosthesis delivery.

9. The vascular prosthesis delivery device of claim 8, wherein the distal enlargement is smaller than the larger inner diameter section of the tip member, but larger than the smaller diameter section of the tip member.

10. The vascular prosthesis delivery device of claim 8, wherein the pusher element has recesses accommodating bulbs on a proximal end of the prosthesis.

11. The vascular prosthesis delivery device of claim 8, wherein the tip member has recesses accommodating bulbs on a distal end of the prosthesis.

12. A vascular prosthesis delivery device comprising:
an inner tube accommodating a guidewire;
a prosthesis;
a pusher element movable over the inner tube, the pusher element having recesses accommodating a proximal portion of the prosthesis;
a sheath disposed over the inner tube and the pusher element;
a tip member movable over the inner tube, the tip member having an inner passage and recesses accommodating a distal portion of the prosthesis; and
a stop member positioned at a distalmost end of the inner tube and having a diameter larger than the inner tube;
wherein the stop member is configured to pass at least partially within and engage the inner passage of the tip member to limit further movement of the tip member during prosthesis delivery from the sheath.

13. The vascular prosthesis delivery device of claim 12, wherein the inner passage of the tip member has a smaller inner diameter section and a larger inner diameter section.

14. The vascular prosthesis delivery device of claim 12, further comprising a pusher rod connected to the pusher element and capable of displacing the pusher element over the inner tube.

15. The vascular prosthesis delivery device of claim 14, wherein the pusher element has a slot accommodating the pusher rod.

* * * * *